United States Patent [19]

Luzzi et al.

[11] Patent Number: 5,147,568

[45] Date of Patent: Sep. 15, 1992

[54] SUBSTITUTED 2,3-DIHYDROPERIMIDINE STABILIZERS

[75] Inventors: John J. Luzzi, Carmel; David H. Steinberg, Bronx, both of N.Y.

[73] Assignee: Ciba-Geigy Corporation, Ardsley, N.Y.

[21] Appl. No.: 783,946

[22] Filed: Oct. 28, 1991

Related U.S. Application Data

[63] Continuation-in-part of Ser. No. 696,693, May 7, 1991, abandoned.

[51] Int. Cl.$^5$ ................ C10M 105/72; C07D 239/00
[52] U.S. Cl. .................................. 252/47; 252/47.5; 252/50; 544/249
[58] Field of Search ............... 252/47, 50; 544/231, 544/249

[56] References Cited

U.S. PATENT DOCUMENTS

| | | | |
|---|---|---|---|
| 3,185,538 | 5/1965 | Voltz | 544/249 |
| 3,509,214 | 4/1970 | Braid | 252/50 |
| 3,535,243 | 10/1970 | Chao | 252/50 |
| 3,573,206 | 3/1971 | Braid | 252/50 |
| 4,224,071 | 9/1980 | Buell | 544/249 |
| 4,224,326 | 9/1980 | Matsumoto | 544/249 |
| 4,294,964 | 10/1981 | Matsumoto | 544/249 |
| 4,389,321 | 6/1983 | Malherbe | 252/50 |
| 4,565,424 | 1/1986 | Huffman | 252/299.1 |

OTHER PUBLICATIONS

CA 102:6382, Pozharskii et al, *Heterocyclic analogs of pleiadiene*, Zh. Org. Kim., 1984.
CA 95:187,185, Pozharskii et al, *Perinaphthylenediamines*, Zh. Org. Khim. 1981.
R. Gleiter et al., J. Org. Chem. 51, 370 (1986).
A. F. Pozharskii et al., Zh. Org. Khim 17, 1005 (1981).
A. F. Pozharskii et al., Zh. Org. Khim. 20, 1567 (1984).

*Primary Examiner*—Prince Willis, Jr.
*Assistant Examiner*—Thomas Steinberg
*Attorney, Agent, or Firm*—Luther A. R. Hall

[57] ABSTRACT

N-Allyl and N-methylene-thio substituted 2,3-dihydroperimidine compounds are very effective antioxidant stabilizers for organic material subject to oxidative or thermal degradation, particularly for lubricant compositions.

17 Claims, No Drawings

SUBSTITUTED 2,3-DIHYDROPERIMIDINE STABILIZERS

This is a continuation-in-part of application Ser. No. 696,693, filed on May 7, 1991, now abandoned.

This invention pertains to N-allyl and N-methylene-thio substituted 2,3-dihydroperimidines and their use as antioxidant stabilizers for lubricant compositions.

BACKGROUND OF THE INVENTION

The use of aromatic amines as stabilizers for lubricant compositions is well-known in the art. U.S. Pat. Nos. 3,509,214 and 3,573,206 typify the state of the art for such products.

It is well-known that many organic liquids and solids used in industrial applications, such as oils and greases, power transmission fluids, resin and polymer coatings, insulations, structural products and the like, may deteriorate when subjected to oxidation. Since these substances are very often used at high temperatures, the rate of oxidative breakdown can be very rapid. This problem is particularly important in the operation of modern day automotive and aircraft engines. The breakdown of the lubricating oil, either natural or synthetic, is frequently accompanied by the formation of corrosive acids, sludge and other breakdown products. These resulting products can harm the metal surfaces of the engine and interfere with the efficient operation of the lubricants.

U.S. Pat. Nos. 3,509,214 and 3,573,206 disclose that the stability of the organic compounds used in such lubricants which are normally susceptible to oxidative deterioration could be unexpectedly improved by the addition thereto of an N-arylnaphthylamine containing lower oligomer obtained by subjecting said N-arylnaphthylamine or mixture of said N-arylnaphthylamine with a diphenylamine or a second N-arylnaphthylamine to either thermal or chemical oxidation or both.

A number of N-alkyl substituted 2,3-dihydroperimidine compounds are known in the prior art as seen below:

J. Org. Chem. 51, 370 (1986) describes 2-chloro-1,3-dimethyl-1H-perimidine;

Zh. Org. Khim. 17, 1005 (1981); Chem. Abst. 95, 187185r describes the general synthetic methods used to prepare 1-alkyl-2,3-dihydroperimidines;

Zh. Org. Khim. 20, 1567 (1984); Chem. Abst. 102, 6382x (1985) describes 2,2'-bis(2,3-dihydroperimidines).

U.S. Pat. No. 4,389,321 describes selected 2,3-dihydroperimidines which are useful as antioxidants for lubricant compositions. Although these compounds are peripherally related to some of the instant compounds, none of the compounds of this reference are substituted on the N-atom with an alkenyl or sulfur-containing moiety.

U.S. Pat. No. 3,185,538 describes various substituted perimidinium halide methine dye salts useful for coloring polyacrylonitrile. U.S. Pat. No. 4,224,071 discloses nitro-substituted monoazo dihydroperimidines which are useful as black dyes for ballpoint pen inks. U.S. Pat. Nos. 4,224,326 and 4,294,964 describe selected 2-aryl-1H-perimidines which are useful as immunosuppresive agents. U.S. Pat. No. 4,565,424 discloses some dichroic poly(arylazo) dyestuffs having inter alia some dihydroperimidine end groups. None of these references describe compounds which are substituted on the N-atom with an alkenyl or sulfur-containing moiety.

The instant invention pertains to N-alkenylated, preferably N-allylated or N-methallylated, and N-methylene-thio substituted 2,3-dihydroperimidines which have been found to have superior antioxidant properties in lubricant compositions.

OBJECTS OF THE INVENTION

One object of the invention is to provide new N-alkenylated or N-methylene-thio substituted 2,3-dihydroperimidine compounds which are effective antioxidants for lubricant compositions.

Another object of this invention is to provide organic lubricant compositions stabilized against thermal or oxidative degradation using an effective stabilizing amount of an N-alkenylated or N-methylene-thio substituted 2,3-dihydroperimidine.

DETAILED DISCLOSURE

The instant invention pertains to an N-substituted 2,3-dihydroperimidine of formula I

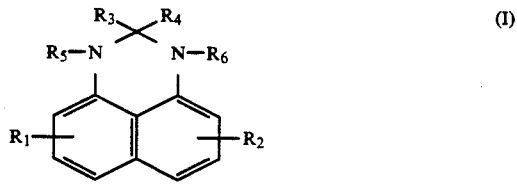

wherein $R_1$ and $R_2$ are independently hydrogen, alkyl of 1 to 12 carbon atoms, alkenyl of 3 to 18 carbon atoms, cycloalkyl of 5 to 12 carbon atoms, phenylalkyl of 7 to 15 carbon atoms or aryl of 6 to 10 carbon atoms, $R_3$ is hydrogen or alkyl of 1 to 12 carbon atoms, $R_4$ is hydrogen, alkyl of 1 to 17 carbon atoms, alkyl of 1 to 4 carbon atoms substituted by phenyl, alkenyl of 2 to 17 carbon atoms, alkenyl of 2 to 4 carbon atoms substituted by phenyl or aryl of 6 to 10 carbon atoms, or $R_3$ and $R_4$ together are straight or branched alkylene of 4 to 11 carbon atoms, and $R_5$ and $R_6$ are independently hydrogen, alkenyl of 3 to 18 carbon atoms, —$CH_2$—S—$E_1$, —$CH_2$—S—$C_nH_{2n}$—S—$E_1$ or —$CH_2$—S—T—$COOE_2$, where n is 2 to 6, $E_1$ is alkyl of 1 to 18 carbon atoms, alkenyl of 3 to 18 carbon atoms, cycloalkyl of 5 to 12 carbon atoms, aryl of 6 to 10 carbon atoms, phenylalkyl of 7 to 9 carbon atoms, or said aryl or said phenylalkyl substituted on the aryl or phenyl moiety by one or two alkyl of 1 to 8 carbon atoms or by hydroxyl and by one or two alkyl of 1 to 8 carbon atoms, $E_2$ is alkyl of 1 to 18 carbon atoms, alkenyl of 3 to 18 carbon atoms, cycloalkyl of 5 to 12 carbon atoms, aryl of 6 to 10 carbon atoms or phenylalkyl of 7 to 9 carbon atoms, and T is methylene, ethylene or ethylidene, with the proviso that $R_5$ and $R_6$ are not both hydrogen at the same time.

Preferably $R_1$ and $R_2$ are independently hydrogen or alkyl of 1 to 4 carbon atoms; most preferably hydrogen.

Preferably $R_3$ and $R_4$ are each hydrogen or are together pentamethylene.

Preferably at least one of $R_5$ and $R_6$ is allyl, methallyl, —$CH_2$—S—$E_1$, —$CH_2$—S—$C_nH_{2n}$—S—$E_1$ or —$CH_2$—S—T—COO—$E_2$ where n is 2, $E_1$ or $E_2$ is alkyl of 2 to 12 carbon atoms, and T is methylene; most preferably allyl, methallyl, —$CH_2$—S—$E_1$ or —$CH_2$—S—T—COO—$E_2$ where $E_1$ or $E_2$ is alkyl of 8 to 12 carbon atoms and T is methylene. Especially preferred are compounds where at least one of $R_5$ and $R_6$ is allyl.

It is understood that a mixture of the instant compounds of formula I having N-alkenyl and/or N-methylene-thio substitution can be used as lubricant antioxidants within the purview of the instant invention.

The N-alkenyl substituted compounds of this invention are conveniently prepared by reaction of a 2,3-dihydroperimidine with an alkenyl halide, such as allyl bromide or methallyl chloride, in the presence of alkali and a quaternary alkylammonium salt. These intermediates are largely items of commerce.

The instant compounds substituted on the N-atom by $—CH_2—S—E_1$, by $—CH_2—S—C_nH_{2n}—S—E_1$ or by $—CH_2—S—T—COO—E_2$ are prepared by a Mannich reaction using 2,3-dihydroperimidine, formaldehyde and a mercaptan or an ester of a mercaptoalkanoic acid, such as a mercaptoacetic, mercaptolactic or 3-mercaptopropionic acid ester. These materials too are largely items of commerce.

Alternatively, the instant compounds substituted on the N-atom by $—CH_2—S—E_1$, by $—CH_2—S—C_nH_{2n}—S—E_1$ or by $—CH_2—S—T—COO—E_2$ are prepared by a Mannich reaction using 1,8-naphthalenediamine, formaldehyde and a mercaptan or an ester of a mercaptoalkanoic acid, such as a mercaptoacetic, mercaptolactic or 3-mercaptopropionic acid ester. These materials are largely items of commerce.

The intermediates for the instant compounds of formula I are formed by reacting 1,8-naphthalenediamine with an appropriate aldehyde (such as formaldehyde or cinnamaldehyde), acyclic ketone (such as methyl ethyl ketone) or cyclic ketone (such as cyclohexanone or cyclododecanone) in the presence of an acid catalyst such as propionic acid, toluenesulfonic acid or trichloroacetic acid.

When any of $R_1$ to $R_6$ or $E_1$ or $E_2$ is alkyl, such alkyl groups are, for example, methyl, ethyl, isopropyl, n-butyl, tert-butyl, tert-amyl, 2-ethylhexyl, n-octyl, lauryl or n-octadecyl; when said radicals are alkenyl, they are for example, allyl, methallyl and oleyl; when said radicals are cycloalkyl, they are, for example cyclopentyl, cyclohexyl, cyclooctyl and cyclododecyl; when said radicals are alkyl substituted by phenyl or phenylalkyl, they are, for example, benzyl, phenethyl, α-methylbenzyl and α,α-dimethylbenzyl; when said radicals are aryl, they are, for example phenyl or naphthyl; or when said radicals are alkenyl substituted by phenyl, they are, for example, cinnamenyl.

The instant invention also relates to lubricant compositions, having improved oxidation or thermal stability, which comprises (a) a major amount of a lubricant, subject to oxidative or thermal degradation, and (b) an effective stabilizing amount of a compound of formula I as described above.

The lubricant of component (a) is particularly a lubricating oil or grease wherein the base medium is a hydrocarbon or synthetic lubricant. The preferred base fluids of this invention include the hydrocarbon mineral oils, olefin fluids, polyolefin fluids, polyether fluids, polyacetals, alkylene oxide polymers, silicone-base fluids and ester fluids. The esters of dicarboxylic acids and monohydric alcohols and the trimethylolpropane and pentaerythritol esters of monocarboxylic acids are particularly of interest. Suitable diesters include the esters of oxalic, malonic, succinic, glutaric, adipic, pimelic, suberic, azelaic and sebacic acids, cyclohexane dicarboxylic acid, phthalic acid, terephthalic acid and the like; and alcohols having 1 to 20 carbon atoms. A commonly used diester is di(2-ethylhexyl)sebacate.

The acids used in forming the trimethylolpropane and pentaerythritol esters include those containing 1 to 30 carbon atoms having straight or branched chain aliphatic, cycloaliphatic, aromatic or alkylated aromatic structures. Mixtures of one or more of such acids may also be used in the preparation of these tri- and tetra-esters. Typical carboxylic acids include, acetic, propionic, butyric, valeric, isovaleric, caproic, caprylic, pelargonic, capric, isodecanoic, lauric, benzoic, nonylbenzoic, dodecylbenzoic, naphthoic, cyclohexanoic and the like. The acids most particularly preferred are pelargonic and commeric valeric acid which contains both n-valeric and isovaleric acids.

The most preferred ester used in this invention is an ester prepared from pentaerythritol, pelargonic, n-valeric and isovaleric acids.

The instant compounds are sufficiently soluble in lubricants to afford the desired antioxidant stabilizing effects. Suitable concentrations range from about 0.001% to about 10% by weight based on the total lubricant composition. Preferably the effective stabilizing amount of the instant compounds is from about 0.1% to about 5% by weight of the total lubricant composition.

The lubricant composition of the instant invention find a wide variety of end uses including engine oils, such as aviation engine oils, automotive engine oils, diesel engine oils, railroad diesel oils, truck diesel oils and the like.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent bright-stocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: $G_1$-OCC-alkylene-COO$G_2$ wherein "alkylene" denotes an alkylene residue having from 2 to 14 carbon atoms and $G_1$ and $G_2$ are the same or different and each is an alkyl group having from 6 to 18 carbon atoms. Tri-esters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of phenolic antioxidants

1. Alkylated Monophenols 2,6-Di-tert-butyl-4-methylphenol, 2,6-di-tert-butylphenol, 2-tert-butyl-4,6-dimethyl-phenol,2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-dimethylphenol, 2,6-di-octa-decyl-4-methylphenol, 2,4,6-tri-cyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexyl-phenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methylphenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants

N,N'-Di-isopropyl-p-phenylenediamine, N,N'-di-sec.-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methylphenol, 2,4'-diamino-diphenylmethane, 4,4'-diamino-diphenyl-methane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allyl-phenothiazine, tert-octylated phenothiazine, 3,7-di-tert-octylphenothiazine.

Examples for other antioxidants:

Aliphatic or aromatic phosphites, esters of thiodipropionic acid or of thiodiacetic acid, or salts of dithiocarbamic or dithiophosphoric acid.

Examples of metal passivators, for example for copper, are:

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

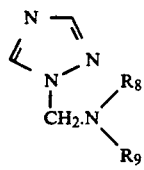

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g.

I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula $$R_{12}-X_2-CH_2-CH(OH)-CH_2NR_{13}R_{14}$$

in which $X_2$ is $-O-$, $-S-$, $-SO_2-C(O)-O-$ or $-N(Rd)$ in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstitued $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl $-CH_2-CH(OH)-CH_2NR_{13}R_{14}$ or $R_{12}$ is $C_2-C_{18}$alkenyl, $C_2-C_3$alkynyl or $C_5-C_{12}$cycloalkyl provided that, when $X_2$ is $-O-$ or $-C(O)-O-$, $R_{12}$ is branched $C_4-C_{20}$alkyl. These compounds are described in GB Patent Specification 2172284A.

h) Compounds having the formula:

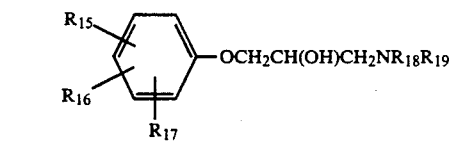

in which $R_{15}$, $R_{16}$, $R_{17}$ are, independently, hydrogen, $C_1-C_{15}$alkyl, $C_5-C_{12}$cycloalkyl, $C_6-C_{15}$aryl or $C_7-C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are:

Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are:

Polymethacrylates, alkylated naphthalene derivatives.

Examples of dispersants/detergents are:

Polybutenylsuccinic acid-amides or -imides, polybutenyl-phosphonic acid derivatives, basic magnesium-, calcium-, and bariumsulfonates and -phenolates.

Examples of anti-wear additives and extreme pressure additives are:

Sulphur- and/or phosphorus- and/or halogen-conytaining compounds e.g. sulphurised vegetable oils, zinc dialkyldithiophosphates, tritolylphosphate, chlorinated paraffins, alkyl- and aryldi- and trisulphides, triphenylphosphorothionate.

The following examples are presented for the purpose of illustration only and are not to be construed as limiting the nature or scope of the instant invention in any manner whatsoever.

EXAMPLE 1

1,3-Di(n-octylthiomethyl)-2,3-dihydroperimidine

To a 500-ml flask fitted with a stirrer, thermometer, condenser and nitrogen inlet are added 7.9 g (0.05 m) of 1,8-naphthalenediamine, 14.6 g (0.1 m) of n-octyl mercaptan, 25.0 g (0.3 m) of 37% aqueous formaldehyde solution and 75 ml of methanol. The reaction mixture is heated to reflux for six hours. At the end of this period a test thin layer chromatogram indicates that most of the 1,8-naphthalenediamine and n-octyl mercaptan have reacted. Heating is then stopped and the solution allowed to cool with stirring overnight. The reaction mixture is then transferred to a separatory funnel with ether and water. The organic layer is separated, washed with water and then dried over anhydrous sodium sulfate. The solvent is then removed under reduced pressure and the crude residue is purified by flash chromatography using silica gel. The fraction containing the desired product is recrystallized from petroleum ether to afford 5.9 g of the title compound as white crystals melting at 52°–56° C.

Analysis: Calcd for $C_{29}H_{46}N_2S_2$: C, 71.5; H, 9.5; N, 5.7. Found: C, 71.6; H, 9.4; N, 5.6.

EXAMPLE 2

1,3-Di(2-ethylhexyloxycarbonylmethylthiomethyl)-2,3-dihydroperimidine

Following the general method of Example 1, and substituting and equivalent amount of 2-ethylhexyl mercaptoacetate for n-octyl mercaptan, the above-named compound is obtain as a violet oil.

Analysis: Calcd for $C_{33}H_{50}N_2O_4S_2$: C, 65.7; H, 8.4; N, 4.6. Found: C, 65.4; H, 8.2; N, 4.3.

EXAMPLE 3

1-Allyl-2,2-pentamethylene-2,3-dihydroperimidine

Following the general procedure of Example 1 of U.S. Pat. No. 4,389,321, 2,2-pentamethylene-2,3-dihydroperimidine is prepared by the reaction of equimolar amounts of 1,8-naphthalenediamine and cyclohexanone in toluene at reflux temperature.

When 12.1 g (0.1 m) of allyl bromide and 11.9 g (0.05 m) of 2,2-pentamethylene-2,3-dihydroperimidine are dissolved in methylene chloride and then reacted in the presence of 50% aqueous sodium hydroxide solution and 3.4 g (0.01 m) of tetrabutyl ammonium hydrogen sulfate, the title compound is afforded as a violet solid melting at 64°–69° C.

Analysis: Cacld for $C_{19}H_{22}N_2$: C, 82.0; H, 8.0; N, 10.1.

Found: C, 82.3; H, 8.1; N, 9.9.

EXAMPLE 4

1,3-Diallyl-2,2-pentamethylene-2,3-dihydroperimidine

When using the general procedure of Example 3, but employing a 5 to 1 molar ratio of allyl bromide to 2,2-pentamethylene-2,3-dihydroperimidine, the title compound is obtained.

EXAMPLE 5

1,3-Dimethallyl-2,2-pentamethylene-2,3-dihydroperimidine

When using the procedure given in Example 4 and replacing allyl bromide with an equivalent amount of methallyl chloride, the title compound is obtained.

EXAMPLE 6

1,3-Di[2-(n-octylthio)ethylthiomethyl]-2,3-dihydroperimidine

Following the general procedure given in Example 1, the title compound is afforded when 1,8-naphthalenediamine, 37% aqueous formaldehyde and 2-(n-octylthio)ethyl mercaptan are reacted.

The corresponding mono-substituted 2,3-dihydroperimidine is obtained by reducing the molar ratio of mercaptan to diamine.

EXAMPLE 7

The instant compounds are tested for their antioxidant activity in lubricant compositions using the Thin-Film Oxygen Uptake Test (TFOUT) method according to ASTM D4742.

The instant compounds are added at the 0.5% by weight concentration into a standard crankcase formulation (API 1119) whose performance in TFOUT testing is known to correlate well with ultimate engine performance. The longer the time indicated for antioxidant activity indicates a more efficacious stabilizer. The results of these tests are given in the table below.

| 0.5% by weight of Compound of Example | TFOUT Time (minutes) |
| --- | --- |
| None | 110 |
| 1 | 192 |
| 3 | 229 |

Both of the instant compounds show significant antioxidant activity in this standard formulated lubricant composition.

What is claimed is:

1. An N-substituted 2,3-dihydroperimidine of formula I

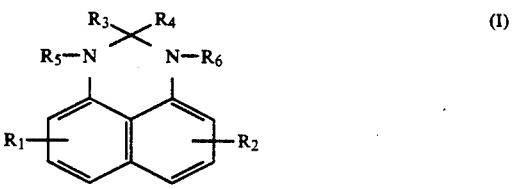

wherein $R_1$ and $R_2$ are independently hydrogen, alkyl of 1 to 12 carbon atoms, alkenyl of 3 to 18 carbon atoms, cycloalkyl of 5 to 12 carbon atoms, phenylalkyl of 7 to 15 carbon atoms or aryl of 6 to 10 carbon atoms, $R_3$ is hydrogen or alkyl of 1 to 12 carbon atoms, $R_4$ is hydrogen, alkyl of 1 to 17 carbon atoms, alkyl of 1 to 4 carbon atoms substituted by phenyl, alkenyl of 2 to 17 carbon atoms, alkenyl of 2 to 4 carbon atoms substituted by phenyl or aryl of 6 to 10 carbon atoms, or $R_3$ and $R_4$ together are straight or branched alkylene of 4 to 11 carbon atoms, and $R_5$ and $R_6$ are independently hydrogen, alkenyl of 3 to 18 carbon atoms, $-CH_2-S-E_1$, $-CH_2-S-C_nH_{2n}-S-E_1$ or $-CH_2-S-T-COOE_2$, where n is 2 to 6, $E_1$ is alkyl of 1 to 18 carbon atoms, alkenyl of 3 to 18 carbon atoms, cycloalkyl of 5 to 12 carbon atoms, aryl of 6 to 10 carbon atoms, phenylalkyl of 7 to 9 carbon atoms, or said aryl or said phenylalkyl substituted on the aryl or phenyl moiety by one or two alkyl of 1 to 8 carbon atoms or by hydroxyl and by one or two alkyl of 1 to 8 carbon atoms, $E_2$ is alkyl of 1 to 18 carbon atoms, alkenyl of 3 to 18 carbon atoms, cycloalkyl of 5 to 12 carbon atoms, aryl of 6 to 10 carbon atoms or phenylalkyl of 7 to 9 carbon atoms, and T is methylene, ethylene or ethylidene, with the proviso that $R_5$ and $R_6$ are not both hydrogen at the same time.

2. A compound according to claim 1 where $R_1$ and $R_2$ are independently hydrogen or alkyl of 1 to 4 carbon atoms.

3. A compound according to claim 2 wherein $R_1$ and $R_2$ are each hydrogen.

4. A compound according to claim 1 wherein $R_3$ and $R_4$ are each hydrogen or are together pentamethylene.

5. A compound according to claim 1 wherein at least one of $R_5$ and $R_6$ is allyl, methallyl, $-CH_2-S-E_1$, $-CH_2-S-C_nH_{2n}-S-E_1$ or $-CH-$ 2—S—T—COO—E$_2$ where n is 2, E$_1$ or E$_2$ is alkyl of 2 to 12 carbon atoms, and T is methylene.

6. A compound according to claim 5 wherein at least one of R$_5$ and R$_6$ is allyl, methallyl, —CH$_2$—S—E$_1$ or —CH$_2$—S—T—COO—E$_2$ where E$_1$ or E$_2$ is alkyl of 8 to 12 carbon atoms and T is methylene.

7. A compound according to claim 6 wherein at least one of R$_5$ and R$_6$ is allyl.

8. The compound according to claim 1 which is 1,3-di(n-octylthiomethyl)-2,3-dihydroperimidine.

9. The compound according to claim 1 which is 1,3-di(2-ethylhexyloxycarbonylmethylthiomethyl)-2,3-dihydroperimidine.

10. The compound according to claim 1 which is 1-allyl-2,2-pentamethylene-2,3-dihydroperimidine.

11. The compound according to claim 1 which is 1,3-diallyl-2,2-pentamethylene-2,3-dihydroperimidine.

12. The compound according to claim 1 which is 1,3-dimethallyl-2,2-pentamethylene-2,3-dihydroperimidine.

13. The compound according to claim 1 which is 1,3-di[2-(n-octylthio)ethylthiomethyl]-2,3-dihydroperimidine.

14. A lubricant composition, stabilized against thermal or oxidative degradation, which comprises
(a) a major amount of a lubricant, subject to oxidative or thermal degradation, and
(b) an effective stabilizing amount of a compound of formula I according to claim 1.

15. A composition according to claim 14 wherein the compound of component (b) is 1,3-di(n-octylthiomethyl)-2,3-dihydroperimidine.

16. A composition according to claim 14 wherein the compound of component (b) is 1-allyl-2,2,-pentamethylene-2,3-dihydroperimidine.

17. A composition according to claim 14 wherein the compound of component (b) is selected from the group consisting of
1,3-di(2-ethylhexyloxycarbonylmethylthiomethyl)-2,3-dihydroperimidine;
1,3-diallyl-2,2-pentamethylene-2,3-dihydroperimidine;
1,3-dimethallyl-2,2-pentamethylene-2,3-dihydroperimidine; and
1,3-di-2,3-dihydroperimidine.

* * * * *